United States Patent [19]

McMillan

[11] Patent Number: 4,951,684
[45] Date of Patent: Aug. 28, 1990

[54] DEVICE FOR COLLECTING BIOLOGICAL MATERIAL

[75] Inventor: William A. McMillan, Cupertino, Calif.

[73] Assignee: Syntex (U.S.A.) Inc., Palo Alto, Calif.

[21] Appl. No.: 326,138

[22] Filed: Mar. 20, 1989

Related U.S. Application Data

[63] Continuation of Ser. No. 50,848, May 15, 1987, abandoned.

[51] Int. Cl.⁵ .............................................. A61B 10/00
[52] U.S. Cl. .................................................. 128/758
[58] Field of Search ............... 128/304, 757, 758, 357; 435/292; 604/22

[56] References Cited

U.S. PATENT DOCUMENTS

| | | |
|---|---|---|
| D. 219,252 | 11/1970 | Bogoff . |
| D. 251,013 | 2/1979 | Kettel . |
| D. 264,246 | 5/1982 | Ekbladh et al. . |
| D. 271,519 | 11/1983 | Baitz . |
| D. 274,464 | 6/1984 | Baitz . |
| D. 275,127 | 8/1984 | Edwards . |
| 752,356 | 2/1904 | Pilling . |
| 2,437,329 | 3/1948 | Moore . |
| 2,495,794 | 1/1950 | Weller . |
| 2,778,357 | 1/1957 | Leibinger et al. . |
| 2,876,777 | 3/1959 | Kees, Jr. . |
| 3,234,107 | 2/1966 | Kaufman et al. . |
| 3,455,788 | 7/1969 | Curry et al. . |
| 3,626,470 | 12/1971 | Antonides et al. . |
| 3,635,222 | 1/1972 | Robinson . |
| 3,661,144 | 5/1972 | Jensen et al. . |
| 3,828,765 | 8/1974 | McDonald . |
| 3,838,681 | 10/1974 | Dalton ................................ 128/757 |
| 3,850,754 | 11/1974 | Wilkens et al. . |
| 4,020,847 | 5/1977 | Clark, III . |
| 4,027,658 | 6/1977 | Marshall ........................ 128/304 X |
| 4,043,322 | 8/1977 | Robinson ............................ 128/758 |
| 4,378,811 | 4/1983 | Levitan . |

FOREIGN PATENT DOCUMENTS

| | | |
|---|---|---|
| 705401 | 6/1931 | France ................................ 128/304 |
| 382904 | 11/1932 | United Kingdom . |
| 1192654 | 5/1970 | United Kingdom . |
| 1208172 | 10/1970 | United Kingdom . |
| 1296008 | 10/1972 | United Kingdom . |

OTHER PUBLICATIONS

Sklar Quality Surgical Instruments Catalog, pp. 345–346, 1975.

Primary Examiner—Michael H. Thaler
Attorney, Agent, or Firm—Carol J. Roth; Theodore J. Leitereg; John A. Dhuey

[57] ABSTRACT

A device for collecting biological material is disclosed. The device comprises a shaft with a loop-like collection structure at one end. The collection structure provides a non-cutting, scraping edge to allow collection of the material without cutting. In a preferred embodiment, the collection means retains the material by diverting it into the interior portion of the collection means. The biological material is released from the device by rotation of the shaft or by elution in an appropriate solvent.

39 Claims, 3 Drawing Sheets

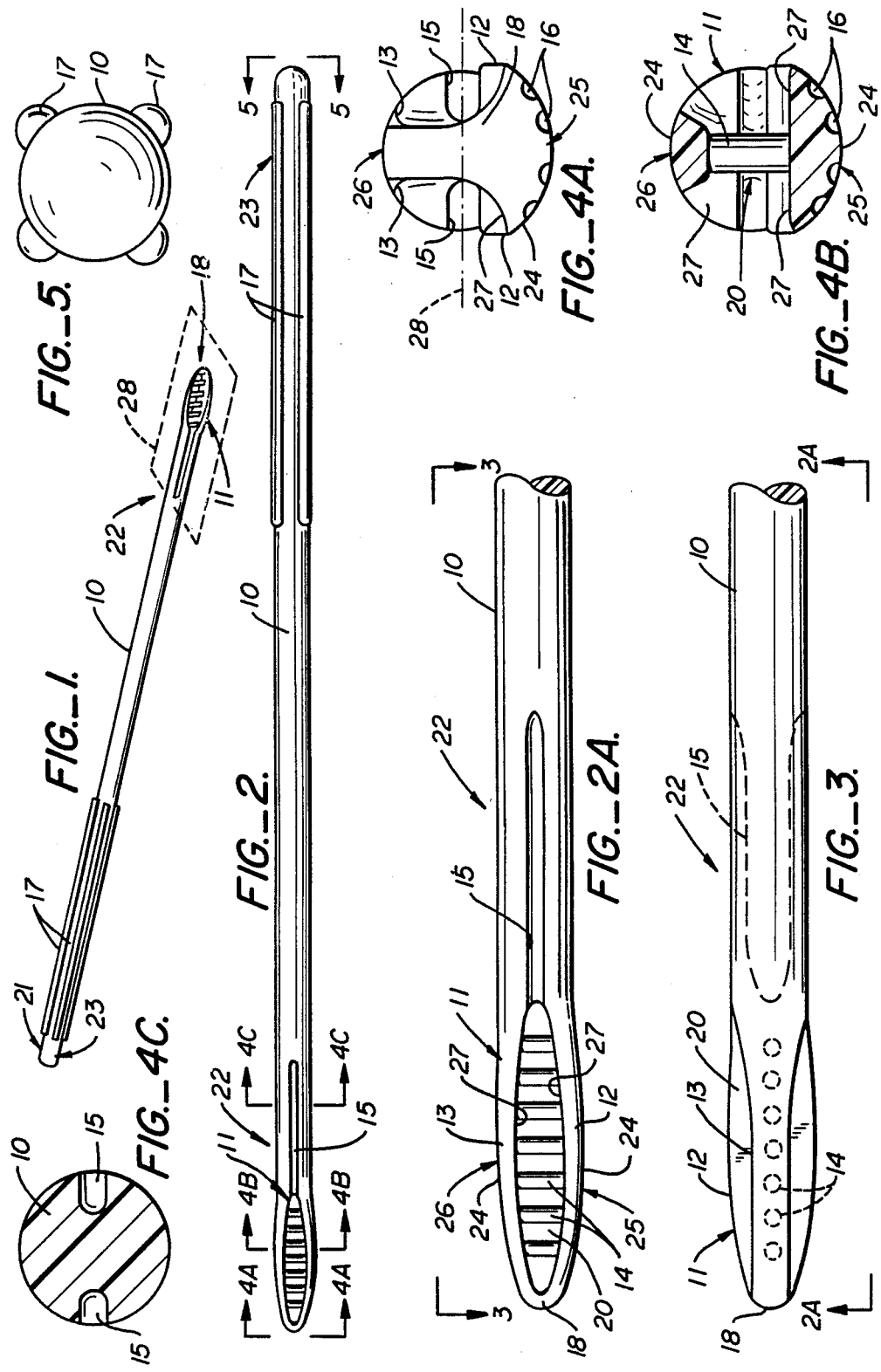

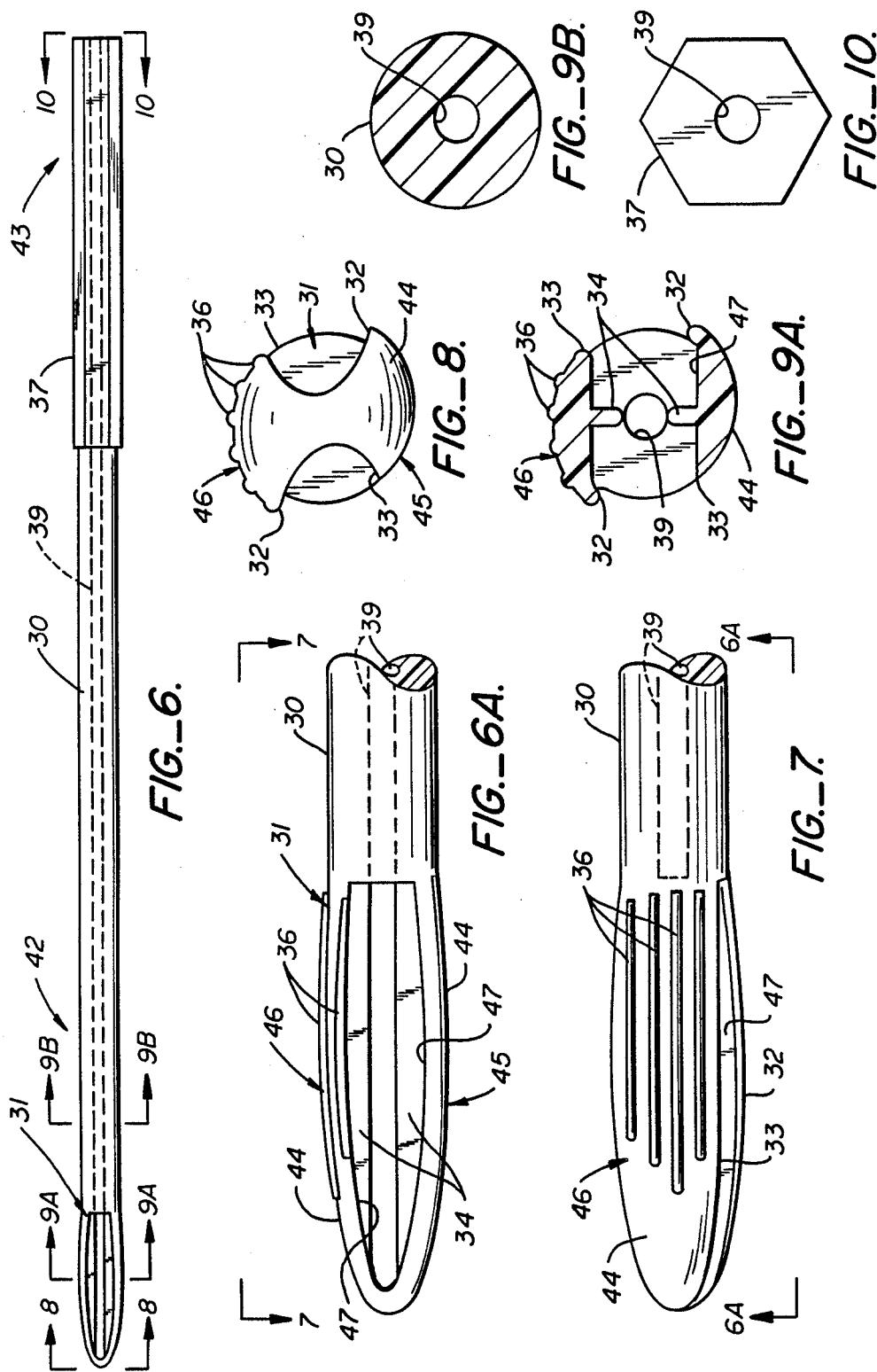

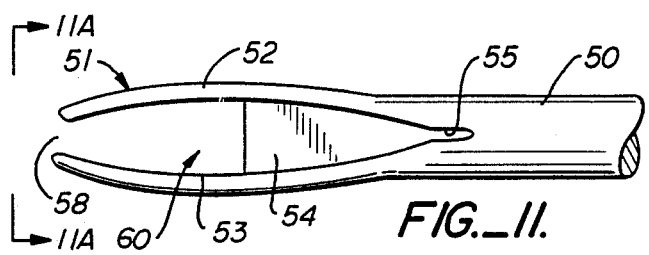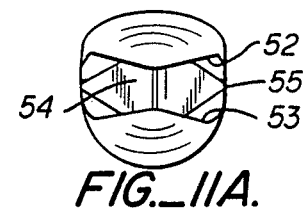
FIG._11.   FIG._11A.
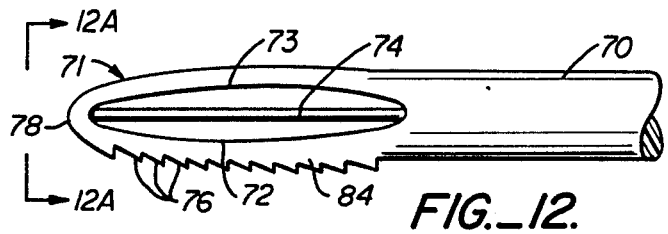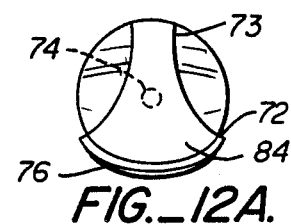
FIG._12.   FIG._12A.
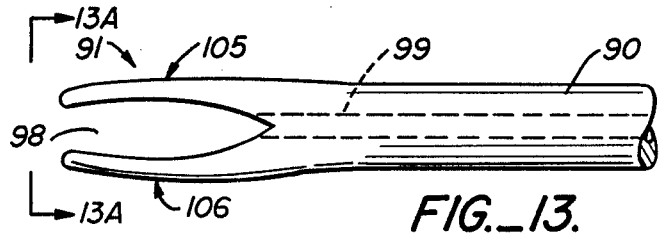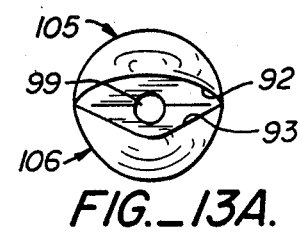
FIG._13.   FIG._13A.
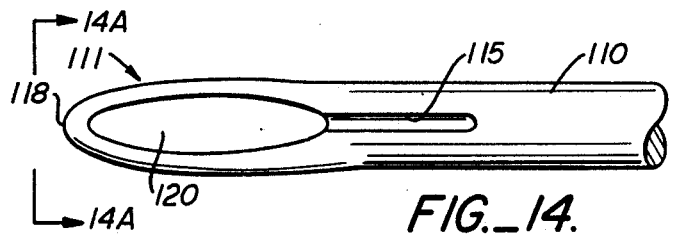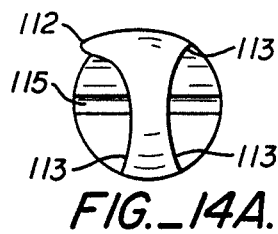
FIG._14.   FIG._14A.
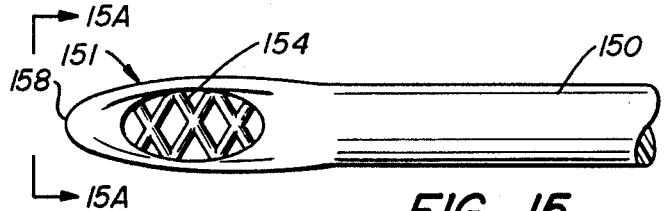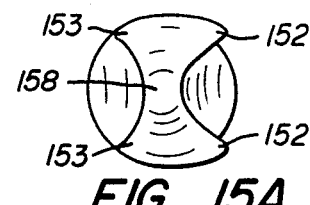
FIG._15.   FIG._15A.
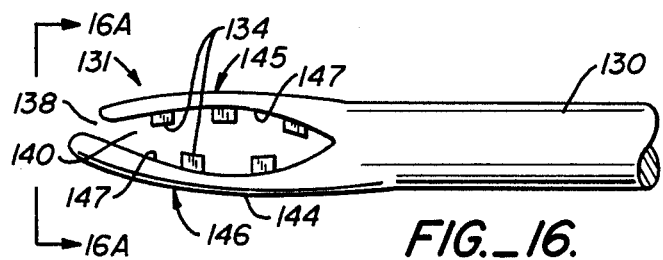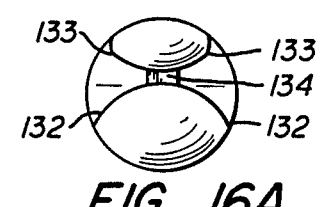
FIG._16.   FIG._16A.

DEVICE FOR COLLECTING BIOLOGICAL MATERIAL

This is a continuation of pending application Ser. No. 07/50,848, filed May 15, 1987, now abandoned incorporated herein by reference.

BACKGROUND OF THE INVENTION

1. Field of Invention

This invention relates to devices for collecting biological samples. The devices are particularly suited for collecting exudates, fluids and columnar epithelium from the endocervix.

Swabs with rough, woven surfaces have been used historically to collect specimens for the analysis of infectious disease from various anatomical sites, including the throat, urethra, vagina, endocervix, rectum and skin. Materials such as cotton, rayon, dacron and nylon were commonly employed as swabs because they absorb significant volumes of fluid and provide for some scraping action.

Swabs are, however, unsuitable for elution methods and for the preparation of direct smears. The absorption and retention properties of swabs and the release properties of swabs are mutually exclusive. A swab made from a material that readily absorbs fluid generally has poor release properties. Therefore, material which is transferred from such a swab to a glass slide contributes significantly to poor assay sensitivity. Furthermore, attempts to elute absorbed material from swabs have shown that, even with the addition of reagents such as detergents, salts and the like to aid elution, the absorption of biological materials by swabs is difficult to reverse. Furthermore, reagents used to chemically actuate elution can actually contribute to the problems associated with loss of antigenic integrity of the subject analyte, toxicity to indicator cell lines in culture tests and an increase in background noise or interference in the assay.

A second problem area relates to specimen quality in terms of how the test material is temporarily absorbed by the swab. For example, as a swab is inserted into the endocervix, it will begin to absorb lumenal material first depending on the viscosity and volume of the contacted material. Thereafter, cellular material and material lining the surface of the endocervix is scraped off as the swab is rotated. The cellular material and the material lining the surface of the endocervix may or may not be absorbed by the swab. Low viscosity lumenal material will reside in the interior of the swab to a greater degree than the superficial epithelial cells and adherent analyte. When the collected material is transferred directly to a glass slide only that part of the specimen on the outside of the swab is transferred. Whereas, if elution is used, extraction of lumenal material from the interior of the swab may also be poor. In those instances wherein lumenal mucus is heavy, access of material to the interior of the swab may be blocked off, thereby effectively stopping absorption early on. Furthermore, the outside of a swab cannot scrap effectively, if covered by a cushion of mucus. The performance of the swab is, therefore, highly dependent on the qualitative and quantitative content of the specimen at the time of sampling. The stage of a disease, such as, for example, chlamydia, and other physiological factors may markedly effect the qualitative content of the specimen at the site.

Metal or plastic bacti loops are often used in place of swabs to obtain urogenital samples for testing sexually transmissible diseases. Metal loops have been used primarily in Europe but for safety reasons are not generally considered acceptable in the United States. The plastic loops available in the United States cannot, in the absence of copious exudate, be relied on to gather sufficient material or to provide for a scraping action as does the swab or, to a lesser extent, the metal loop.

A device called a cytobrush has been used in place of a swab for collecting endocervical samples in nonpregnant patients. The device resembles a miniature bottle cleaning brush and has bristles of various lengths. During collection, biological material including columnar cells adhere to the bristles.

There is a need, therefore, for a collection device that will allow scraping of a surface to collect material without cutting, and will retain the sample material, including both lumenal and scraped material, during and after collection of the specimen. Additionally, such a device will provide consistent quantitative sampling and substantially complete quantitative release during elution.

2. Description of the Prior Art

U.S. Pat. No. 4,020,847 discloses a rotating cutter catheter with a straight cutting edge configured to cut only protruding irregularities along non-desquamating endothelial lining of blood vessels without sampling the intact, normal surface. U.S. Pat. No. 2,437,329 discloses a surgical instrument for curetting having a longitudinal opening formed in the wall of the tube. One lip of the longitudinal opening is everted to form a curetting member. A rectal scraper is disclosed in U.S. Pat. No. 2,495,794. U.S. Pat. No. 3,626,470 discloses a diagnostic device for obtaining cytological samples. The device has an elongated handle with a flexibly coupled platform with a spongelike pledget. A cutting tool and a biopsy punch as disclosed in U.S. Pat. Nos. 2,876,777 and 2,778,357, respectively. Inoculation devices are disclosed in U.S. Pat. Nos. 3,850,754, 3,455,788 and 3,234,107.

Curettes are disclosed in U.S. Pat. No. Des. 275,127 and 219,252. Inoculating loops are disclosed in U.S. Pat. Nos. Des. 274,464 and 271,519. A surgical aspiration catheter and a disposable loop are disclosed in U.S. Pat. Nos. Des. 264,246 and 251,013, respectively.

SUMMARY OF THE INVENTION

The present invention is a device for collection of biological material. The collection device comprises a shaft which has a loop-like collection means at one of its ends. The collection means provides a non-cutting scraping edge.

The collection device of the present invention has the advantage of being contoured to permit optimal sampling over a dimensional anatomical range. Additionally, the device allows for scraping without cutting and has an internal capacity suitable for collection and retention of a large sample. The overall dimensional configuration of the device permits efficient retention of the sample during and after collection and allows release of substantially all of the collected material by rotation of the shaft with or without elution in an appropriate solvent.

BRIEF DESCRIPTION OF THE DRAWINGS

FIG. 1 is a perspective view of a device in accordance with one embodiment of the present invention.

FIG. 2 is a side elevation of the device of FIG. 1.

FIG. 2A is an enlarged side elevation of a portion of the device taken along lines 2A—2A of FIG. 3.

FIG. 3 is an enlarge top plane view of the device taken along lines 3—3 of FIG. 2A.

FIG. 4A is a front elevation of the device taken along lines 4A—4A of FIG. 2.

FIG. 4B is a cross-section of the device taken along lines 4B—4B of FIG. 2.

FIG. 4C is a cross-section of the device taken along lines 4C—4C of FIG. 2.

FIG. 5 is a rear elevation of the device taken along lines 5—5 of FIG. 2.

FIG. 6 is a perspective view of another embodiment of the present invention.

FIG. 6A is an enlarge side elevation of the device taken along lines 6A—6A of FIG. 7.

FIG. 7 is an enlarge top plan view of the device taken along lines 7—7 of FIG. 6A.

FIG. 8 is a front elevation of the device taken along lines 8—8 of FIG. 6.

FIG. 9A is a cross-section of the device taken along lines 9A—9A in FIG. 6.

FIG. 9B is a cross-section of the device taken along lines 9B—9B in FIG. 6.

FIG. 10 is a rear elevation of the device taken along lines 10—10 of FIG. 6.

FIG. 11 is an enlarged side elevation of the distal end of another embodiment of a collection device of the present invention.

FIG. 11A is a top plan view taken along lines 11A—11A of the device of FIG. 11.

FIG. 12 is an enlarged side elevation of the distal end of still another embodiment of a collection device of the present invention.

FIG. 12A is a top plan view taken along lines 12A—12A of the device of FIG. 12.

FIG. 13 is an enlarged side elevation of the distal end of another embodiment of a collection device of the present invention.

FIG. 13A is a top plan view taken along lines 13A—13A of the device of FIG. 13.

FIG. 14 is an enlarged side elevation of the distal end of yet another embodiment of the collection device of the present invention.

FIG. 14A is a top plan view taken along lines 14A—14A of the device of FIG. 14.

FIG. 15 is an enlarged side elevation of the distal end of another embodiment of the device of the present invention.

FIG. 15A is a top plan view taken along lines 15A—15A of the device of FIG. 15.

FIG. 16 is an enlarged side elevation of the distal end of another embodiment of the collection device of the present invention.

FIG. 16A is a top plan view taken along lines 16A—16A of the device of FIG. 16.

DESCRIPTION OF THE SPECIFIC EMBODIMENTS

The device of the present invention is useful for collecting and dispensing biological material. In its broadest aspect of the collection device comprises a shaft which has a loop-like collection means at one end of the shaft. The collection means provides a non-cutting scraping edge.

The device of the present invention is particularly suited for collecting and dispensing endocervical specimens. However, any biological material, for example exudates, fluids, cells, and the like may be collected and dispensed using a device in accordance with the present invention. Such material may be collected from various anatomical sites including, but limited to, the throat, urethra, vagina, rectum, skin, and the like.

In one embodiment of the present invention, the device comprises a shaft having a loop-like collection means at one end. The end at which the collection means is located is generally referred to as the distal end of the shaft. The collection means has a substantially non-cutting edge that scraps biological material and retains it by diverting it into an interior portion of the collection means. The loop-like collection means may have a variety of different shapes. By way of example, but not limitation, the loop-like collection means may be round, oval, elliptical or elongated. The loop-like collection means is preferably elongated. Generally, the loop-like collection means has two sections, a first section and a second section. The first and second sections are defined by a reference plane containing he shaft and perpendicular to a plane passing through the distal end of the collection means and perimeter of the collection means. Each section has an external surface and an internal surface. The external surface may be arched. At least one of the sections may be spoon-like. At least one of the sections has a non-cutting scraping edge. The non-cutting scraping edge is generally defined by the junction of the arched surface of the collection means and its opposed internal surface. The term "loop-like" is used herein to mean a three-dimensional structure that bends so as to form a closed or a partially open curve within itself through which an object can be passed. The end of the loop-like collection means which may be closed or open is preferably rounded and blunt.

The shaft of the present invention is elongated and is preferably substantially rigid. The shaft may be either solid or hollow. In those cases wherein the shaft is solid, the device is useful for passive sampling. In those instances where the shaft is hollow, the device is useful for active sampling and may be adapted to attach to a source or irrigation or suction at or near the proximal end of the shaft. The shaft may have a means for grasping the device near or at its proximal end. The proximal end is that end of the shaft opposed to the collection means. By way of example, but not limitation, such grasping means may include at least one rib or ridge on the external surface of the shaft, a textured surface, or at least one groove on the external surface of the shaft.

The scraping edge of the present invention scrapes material to be collected without cutting the surrounding tissue. In one aspect, the scraping edge comprises at least one leading edge. The term "leading edge" is used herein to refer to one or more edges which protrude beyond the other edge or edges (referred to as the trailing or non-scraping edge or edges) and thereby aid the diversion of material into the interior of the collection means when the shaft is rotated. In cases where the device has two leading edges, they may be positioned so as to be sequential or consecutive, thereby allowing collection of material when he device is rotated in either a clockwise or a counter-clockwise direction. Alternatively, in those instances wherein clockwise or counter-clockwise rotation is preferred, the device may have two leading edges that are non-sequential or non-consecutive. The term "trailing edge" is used herein to refer to one or more edges that are not leading edges and do not protrude.

The end on the tip of the loop-like collection means of the present invention is rounded to prevent cutting of material. The end may be open or closed. Preferably, the end will be open or, if closed, will be as narrow as practical so as to facilitate the flow and collection of material.

Further, the device may include sample retention means mounted within the collection means. The retention means may be attached to the internal surface of at least one section of the collection means. Retention means include by way of example, but not by way of limitation, a grate-like structure, a web-like structure, a fin-like structure, tooth-like or toadstool-like means, ridges, or a septum protruding from at least one internal surface of the collection means and means including at least one member extending between opposed sides of the internal surface of the collection means.

The external surface of the collection means of the present invention may also include a scraping means. Such scraping means include but are not limited to a textured surface, such as a saw-toothed pattern, at least one ridge, or at least one groove. The scraping means may be axially parallel or perpendicular to the central axis of the shaft of the device. On the other hand, the pattern of the scraping means may be random, for example, a textured surface. The scraping means may cover the entire external surface of the collection means or a portion thereof.

The device of the present invention may optionally include an air channel. The term "air channel" is used herein to indicate a means for allowing the release of air from the interior portion or space of the collection means during collection of biological material. Preferably, the air channel will comprise at least one longitudinal groove extending a portion of the length of the shaft near or at the distal end thereof and will communicate with the interior space or portion of the collection means.

The device of the present invention may be adapted to be inserted into a body orifice of a patient to collect the material by scraping without substantially altering the material being collected. In one instance, the device is adapted to collect the material by encasing lumenal matter. The phrase "encasing lumenal matter" is used herein to mean efficiently capturing or enclosing lumenal contents without altering its quality.

In one aspect, the device is adapted to allow the release of substantially all of the collected material from the interior portion of the loop. Preferably, the device is adapted to release the material without substantially altering it. By this is meant that the collected material is released in such a way as to generally maintain the integrity of the collected material. The collected material may be released without substantially altering it by rotating the shaft of the device. Preferably the collected material is released without elution. In some cases, the material may be released by placing the collection means in a liquid and rotating the shaft. To facilitate removal of collected material, the device of the present invention may be comprised of reversibly wettable plastic material or be subjected to surface treatment. Such surface treatment techniques include, but are not limited to plasma surface treatment, flame treatment, corona discharge, or a chemical bath. In a preferred embodiment the internal surface of the collection means are subjected to plasma surface treatment. Information concerning plasma surface treatment is found in *Plastics Technology*, 28:23–26 (1982) which is incorporated by reference herein.

The device may be made of a variety of materials including metals and plastics, including polymers such as polycarbonate, polyethylene, nylon and copolymers thereof. Preferable materials include reversibly wettable plastics. The material selected should be medically acceptable and should not have any adverse effects on the biological material being collected.

The collection device in accordance with the present invention can be further illustrated by reference to the attached drawings.

FIGS. 1–5 are illustrative of one embodiment of a collection device in accordance with the present invention. Now referring to FIGS. 1–5, shaft 10 is preferably substantially rigid and generally has a uniform cross-section. The shaft has a distal end 22 and a proximal end 23. The shaft as shown is solid; therefore, the collection device is suitable for passive collection of biological material. The shaft may be provided with a means 17 for grasping the collection device. The device as illustrated is optionally provided with ribs or ridges for grasping the collection device.

Continuing to refer to FIGS. 1–5, the shaft 10 has a collection means 11 at its distal end 22. The collection means 11 includes at least one non-cutting scraping edge 12 adapted to divert biological material into the interior 20 of the collection means and at least one non-scraping or trailing edge 13. As shown in the present embodiment, the collection means is an elongated loop-like means comprised of a first section 25, a second section 26 and a closed end 18 and defining an interior space or portion 20. The first section 25 and the second section 26 are defined by a reference plane 28 passing through the proximal end 21 and the distal end 18 of the collection means 11. Each section has an internal surface 27 and an external surface 24. At least one of the external surfaces is arched such that the junction of the arched surface and its opposed internal surface define a non-cutting scraping edge 12. As illustrated, the first and second sections are spoon-like.

The dimensions of the collection means are dependent on the anatomical site from which the sample is to be collected and the amount of material needed to complete the test. Generally, however, the collection means will have an internal volume of 10 μl to 1,000 μl, preferably to 10 μl to 500 μl. In those embodiments where the device of the present invention is adapted for collection of endocervical specimens, the collection means will generally have an internal volume of 75 μl to 500 μl and preferably 100 μl to 150 μl. The distal end 18 as illustrated is closed, rounded and blunt. The width of the closed distal end 18 or tip of the collection means will vary depending on the nature of the sample and the anatomical site from which the specimen will be collected. However, generally the width of the closed end generally is 0.25 mm to 2.5 mm and preferably 0.5 mm to 1 mm. In those embodiments having a closed end, the end will generally be as narrow as is practicable so as to allow the material to flow easily around the end. As discussed below, the distal end 18 may also be open. The dimensions and the shape of the end, including determination as to whether the end will be open or closed, will be selected to accommodate various factors including the quantity of material to be collected, the type of material to be collected and the anatomical site from which the material will be collected.

As illustrated in FIGS. 1–5, in a preferred embodiment the collection means 11 is provided with two leading or scraping edges 12 sequentially or consecutively located so as to allow collection of material when the shaft is rotated in either a clockwise or counterclockwise direction. As depicted, the collection device also has two non-scraping or trailing edges 13. In such an embodiment, the two scraping edges 12 protrude more than the two non-scraping edges 13 and the surface area 25 of the first section 25 of the collection means 11 is greater than the surface area 26 of the second section of the collection means 11.

Continuing to refer to FIGS. 1–5, the shaft 10 of the device preferably includes an air channel 15. The air channel is a means for receiving air trapped in the collection means 11 and for moving it away from the collection means during sampling. The air channel 15 as shown in the present embodiment of the device is a groove that extends a portion of the length of the shaft 10 and communicates with the interior space 20 of the collection means 11.

Additionally, sample retention means 14 may optionally be provided within the collection means 11. The sample retention means 14 of the device is mounted within the collection means and may be attached to or integrally formed with at least one internal surface of one section of the collection means 11 and protrude into the interior portion 20 of the collection means 11. Preferably one member extending between opposed sides of the collection means. As is shown in the embodiment illustrated in FIGS. 1–5, the retention means 14 may be grate-like. As illustrated in FIG. 6A, retention means 34 may include one or more ridges of fins mounted on internal surface 47 of at least one section 45 or 46 of collection means 31. As shown in FIG. 11, retention means 54 include a wall or septum mounted within collection means 51, or as shown in FIG. 12 retention means 74 may be substantially parallel to a reference plane passing through the distal end of the shaft and the perimeter of collection means 71. As shown in FIG. 15, retention means 154 may be web-like. As illustrated in FIG. 16, retention means 134 may be tooth-like and protrude into the interior of the collection means 140 without extending between opposed sides of the collection means 140. The illustrations of retention means in the figures are made by way of example and not by way of limitations other means for providing retention of the material will be suggested to those skilled in the art.

Additionally, one or more scraping means 16 may be included on the external surface 24 at least one section 25 or 26 of the collection means 11. Exemplary of such scraping means are textured surfaces, ridges, grooves, and the like. The scraping means 16 may be parallel or perpendicular to the longitudinal axis of the shaft. The scraping means 16 may also be randomly placed. As shown in FIGS. 4A and 4B, preferred scraping means 16 includes texturing external surface 24 of collection means 11. In FIG. 12, preferred scraping means includes saw-tooth like members 76. Other scraping, noncutting means will be suggested to those skilled in the art.

Another preferred embodiment of the present invention is depicted in FIGS. 6–10. The numbering convention used in FIGS. 6–10 have been designed so that the second digit of the number is the same as the second digit of the number of the corresponding element found in the collection device depicted in FIGS. 1–5. Referring to FIGS. 6–10, shaft 30 has a distal end 42 and proximal end 43. Shaft 30 has a passage 39 and may be attached to a suction or irrigation device (not illustrated) at or near proximal end 43. Thus, the device may be used for both passive or active collection of material.

Shaft 30 has a collection means 31 at the distal end 42. The collection means 31 has a first section 45 and a second section 46 defined by a central longitudinal axis of the shaft bisecting the perimeter of the collection means. Each section has an internal surface 47 and an external surface 44. The device, as illustrated, has two leading or scraping edges 32 and two trailing or non-scraping edges 33. In a preferred embodiment, as illustrated, the leading edges are arranged non-sequentially or non-consecutively, so as to allow collection of material when the shaft 30 is rotated in a clockwise direction. It is also envisioned, and well within the invention, that the leading edges 32 may be arranged non-sequentially so as to provide scraping edges so that material is collected when the device is rotated in a counter-clockwise direction.

As mentioned above, the embodiment of the device illustrated in FIGS. 6–10 has sample retention means 34 which one fin-like ridges and are mounted on at least one internal surface 47 of one section 45 or 46 of collection means 31.

As discussed above scrapping means may be provided on one or both external surfaces of the collection means. As shown, scraping means 36 may be included on the external surface 44 of at least one of the external surfaces 44 of the sections 45 or 46 of the collection means. As suggested above, the scraping means can include any noncutting, scraping configuration such as, but not limited to, ridges, grooves, textured surfaces and the like.

Additional embodiments of the collection device are illustrated in FIGS. 11–16A. The numbering convention used in FIGS. 11–16A have been designed so that the final digit of the number is the same as the second digit of the number of the corresponding element of the device dipicted in FIGS. 1–5.

Now referring to FIGS. 11 and 11A, the device of the present invention has a shaft 50 with a collection means 51 at one end. The collection means 51 has leading edge 52 and trailing edge 53. As further illustrated in FIG. 11, the distal end 58 of the collection means 51 is open to facilitate collection of material. Collection means 51 has retention means 54 extending between interior surfaces of opposed sides of the collection means. FIG. 11 also illustrates optional air channel 55 for receiving air trapped in the collection means 51. The air channel 55 communicates with the interior space 60 of the collection means 51 and facilitates the movement of air way from the interior of the collection means 51 during sampling.

Referring to FIGS. 12 and 12A, the device of the present invention has shaft 70 with collection means 71. The end 78 of collection means 71 is closed. As depicted, the collection means 71 has leading or scraping edge 72 and trailing edge 73. The external surface 84 of the collection means 71 has optional scraping means 76. The scraping means 76 as illustrated is in a saw-toothed pattern and may be on the external surface of one or both sections of the collection means. Additionally, the device has a retention means 74 which is substantially parallel to the shaft 70 of the device.

As depicted in FIGS. 13 and 13A, the device of the present invention includes shaft 90 having collection means 91. The shaft has passage 99, therefore, the device may be utilized in active sampling, for example by attachment to a device that provides suction and/or irrigation. The collection means 91 has a first section 105 and second section 106 for retaining the material, a scraping edge 92 and a trailing or nonscraping edge 93. The distal end 98 of collection means 91 is open to facilitate collection of the material. The tips of end 98 are rounded so that the material will be collected without cutting.

Referring now to FIGS. 14 and 14A, the device of the present invention has a shaft 110 and a collection means 111. The collection means 111 has a scraping edge 112 and trailing or nonscraping edges 113. The distal end 118 of the collection means 111 is rounded. Additionally, optional air channel 115 is shown at the distal end of the shaft in communication with the interior 120 of the collection means.

As illustrated in FIGS. 15 and 15A, the distal end 158 of the collection means 151 is closed and the collection means 151 is provided with one leading or scraping edge 152 and three non-scraping edges 153. The scraping edge is located so as to allow collection of material when the shaft is rotated in a clockwise direction. The leading edge 152 can be located so as to allow collection when the device is rotated in a counterclockwise direction. As mentioned above, the retention means 154 of the present invention may be web-like.

As illustrated in FIGS. 16 and 16A, the device of the present invention has a shaft 130 having a collection means 131. The collection means 131 has a first section 145 and a second section 146. Each section has an internal surface 147 and an external surface 144. The collection means 131 has a leading edge 132 and a trailing edge 133 and its distal end 138 is open to facilitate collection of biological material. The tips of the distal end 138 are rounded so that material is collected without cutting. The collection means 131 has retention means 134 attached to the internal surfaces 147 and extending into the interior portion of the collection means 131. As illustrated the retention means 134 do not extend between opposed sides of the collection means.

Collection devices of the present invention can be manufactured from any suitable material. Illustrative considerations for the selection of a suitable material are (a) non-reactivity with an insolubility in the material to be collected, (b) physical properties which allow material to be collected and subsequently released, and (c) sufficient rigidity to allow for manipulation of the device and collection of a sample in accordance with the invention.

As has been mentioned previously, suitable materials include metals such as aluminum, steel, nickel alloys and plastics, such as polycarbonate, polyethylene, nylon and the like and copolymers thereof. It is also contemplated and within the present invention that the physical properties of one or more surfaces of the device be treated to promote retention of the material and/or to facilitate removal of the material. Such treatments include, but are not limited, to plasma surface treatment, flame treatment, corona discharge and chemical baths.

As mentioned earlier, the collection device of the present invention is particularly suited for collecting biological material from a body orifice of a patient. There are a number of instances in which collection of such material is desirable. For example, in diagnostic methods for detecting sexually transmitted diseases a sample of lumenal material may be required. The present device is particularly suited for use in conjunction with the collection of samples for performing an assay. Likewise, the sampling device of the present invention is suitable for use with a diagnostic immunochemical instrument or device.

Therefore, as a matter of convenience, the device of the present invention can be provided in a kit in packaged combination including the device of the present invention and reagents to detect the desired analyte. The kit may also contain an immunochemical instrument or device.

The invention has been described in detail with particular reference to the above embodiments. It will be understood, however, that variations and modifications can be effected within he spirit and scope of the invention.

What is claimed is:

1. A device for collecting biological material adapted to collect said material from a body orifice of a patient comprising:
    an elongated solid shaft member, said shaft member having a distal end, a proximal end and an external surface;
    said distal end of said shaft having a substantially elliptical loop defining an interior space including a first and a second section as defined by a central longitudinal axis of said shaft bisecting the perimeter of said loop, each section having an internal surface and an external surface, wherein at least one of said external surfaces is arched and the junction of said arched surface and its opposed internal surface define a non-cutting scraping edge which is a leading edge when said shaft is rotated; wherein said shaft has at least one longitudinal groove extending a portion of the length of said shaft and communicating with said interior space;
    sample retention means including at least one member extending between the internal surfaces of said loop; and
    wherein said shaft member is in a fixed relationship with said loop.

2. The device of claim 1 including a first and second leading edge wherein said leading edges are not sequential.

3. The device of claim 1 wherein said retention means includes at least one elongated member substantially perpendicular to said central longitudinal axis of said shaft.

4. The device of claim 1 wherein said external surface of at least one section of said loop includes a scraping means in addition to said scraping edge.

5. The device of claim 1 wherein said sample retention means includes a plurality of members parallel to one another.

6. The device of claim 1 wherein said sample retention means includes a plurality of members formed in a web-like pattern.

7. A device for collecting biological material comprising
    a shaft having a distal end and a proximal end, said distal end having a loop-like collection means, and said shaft being in a fixed relationship with said loop-like collection means; wherein said loop-like collection means defines an interior space and said shaft has an external surface defining at least one longitudinal groove extending a portion of the length of said shaft and communicating with said interior space, and wherein said loop-like collection means comprises:

a first section and a second section defined by a reference plane containing said shaft and perpendicular to a plane passing through said distal end and the perimeter of said loop-like collection means, each said section having an external surface and an opposed internal surface; and sample retention means comprising at least one member extending between said internal surfaces of said sections; wherein at least one of said external surfaces is arched and the junction of said arched external surface and said opposed internal surface defines at least one non-cutting scraping edge for scraping and diverting said biological material towards said sample retention means.

8. The device of claim 7 adapted to be inserted into a body orifice of a patient to collect said material without substantially altering material being collected.

9. The device of claim 8 wherein said device is adapted to collect said material by encasing lumenal matter.

10. The device of claim 7 wherein said loop-like collection means is elongated.

11. The device of claim 10 wherein said loop-like arched collection means is substantially elliptical.

12. The device of claim 7 wherein said shaft is substantially rigid.

13. The device of claim 7 wherein said shaft is hollow.

14. The device of claim 13 wherein said shaft is adapted to attach to a source of suction or irrigation.

15. The device of claim 7 wherein said shaft is solid.

16. The device of claim 7 wherein said sample retention means is a web-like structure.

17. The device of claim 7 wherein said sample retention means includes a plurality of elongated members substantially perpendicular to said reference plane.

18. The device of claim 7 wherein said sample retention means includes at least one elongated member substantially parallel to said reference plane.

19. The device of claim 7 wherein said shaft includes means for receiving air trapped in said loop-like collection means and chanelling said air away from said loop-like collection means.

20. The device of claim 7 wherein said non-cutting scraping edge defines a first leading edge when said shaft is rotated.

21. The device of claim 20 wherein said first leading edge diverts said biological material towards said sample retention means.

22. The device of claim 20 wherein said scraping edge defines a first leading edge when said shaft is rotated in a clockwise direction.

23. The device of claim 20 including a second leading edge.

24. The device of claim 23 wherein said first leading edge and said second leading edge are sequential.

25. The device of claim 23 wherein said first leading edge and said second leading edge are not sequential.

26. The device of claim 7 wherein said device is comprised of a polymer selected from the group consisting of polycarbonates, polyethylene, nylons, and others and coplymers thereof.

27. The device of claim 26 wherein said internal surfaces of said loop-like collection means are subjected to plasma surface treatment.

28. The device of claim 7 wherein said device is comprised of a reversibly wettable plastic material.

29. The device of claim 7 further comprising means for grasping said device.

30. The device of claim 7 wherein said device is adapted to release subsequent to collection substantially all of said material from said sample retention means by rotating said shaft.

31. A device for collecting biological material comprising:

a shaft having a distal end and a proximal end, said distal end having a loop-like collection means, and said shaft being in a fixed relationship with said loop-like collection means; wherein said loop-like collection means comprises:

a first section and a second section defined by a reference plane containing said shaft and perpendicular to a plane passing through said distal end and the perimeter of said loop-like collection means, each said section having an external surface and an opposed internal surface; and sample retention means comprising at least one member extending between said internal surfaces of said sections; wherein the surface area of said first section is greater than the surface area of said second section and wherein at least one of said external surfaces is arched and the junction of said arched external surface and said opposed internal surface defines at least lone non-cutting scraping edge for scraping and diverting said biological material towards said sample retention means.

32. The device of claim 31 wherein said loop-like collection means has an open end.

33. The device of claim 31 wherein said loop-like collection means has a closed end and said closed end is round.

34. A device for collecting biological material comprising a shaft having a distal end and a proximal end, said distal end having a loop-like collection means, and said shaft being in a fixed relationship with said loop-like collection means; wherein said loop-like collection means comprises:

a first section and a second section defined by a reference plane containing said shaft and perpendicular to a plane passing through said distal end and the perimeter of said loop-like collection means, each said section having an external surface and an opposed internal surface, and sample retention means comprising at least one elongated member extending between said internal surfaces of said sections; wherein at least one of said elongated members is substantially parallel to said reference plane and wherein at least one of said external surfaces is arched and includes scraping means and the junction of said arched external surface and said opposed internal surface defines at least one non-cutting scraping edge for scraping and diverting said biological material towards said sample retention means.

35. The device of claim 34 wherein said scraping means is a textured surface.

36. The device of claim 35 wherein said textured surface forms a saw-toothed pattern.

37. The device of claim 34 wherein said scraping means comprises at least one ridge.

38. The device of claim 37 wherein at least one of said ridges is substantially axially parallel to said central longitudinal axis of said shaft.

39. The device of claim 34 wherein said scraping means comprises at least one groove.

* * * * *